(12) United States Patent
Braun

(10) Patent No.: US 7,241,288 B2
(45) Date of Patent: Jul. 10, 2007

(54) SURGICAL INSTRUMENT

(76) Inventor: Marcus Braun, Heerstrasse 25, 70563 Stuttgart-Vaihingen (DE)

( * ) Notice: Subject to any disclaimer, the term of this patent is extended or adjusted under 35 U.S.C. 154(b) by 463 days.

(21) Appl. No.: 10/815,394

(22) Filed: Apr. 1, 2004

(65) Prior Publication Data

US 2004/0260334 A1 Dec. 23, 2004

(30) Foreign Application Priority Data

Apr. 1, 2003 (DE) .................... 103 14 828

(51) Int. Cl.
*A61B 17/00* (2006.01)
(52) U.S. Cl. .................... 606/1; 606/205; 606/208
(58) Field of Classification Search .................... 606/1, 606/51–52, 205–208
See application file for complete search history.

(56) References Cited

U.S. PATENT DOCUMENTS

| | | | | | |
|---|---|---|---|---|---|
| 5,174,300 | A | * | 12/1992 | Bales et al. .................. | 600/564 |
| 5,275,608 | A | * | 1/1994 | Forman et al. ............. | 606/170 |
| 5,312,023 | A |   | 5/1994 | Green et al. | |
| 5,330,502 | A | * | 7/1994 | Hassler et al. .............. | 606/205 |
| 5,350,391 | A | * | 9/1994 | Iacovelli ..................... | 606/170 |
| 5,374,277 | A | * | 12/1994 | Hassler ........................ | 606/207 |
| 5,472,451 | A | * | 12/1995 | Freitas et al. ................ | 606/205 |
| 5,474,571 | A | * | 12/1995 | Lang ............................ | 606/205 |
| 5,545,148 | A | * | 8/1996 | Wurster ....................... | 604/223 |
| 5,549,637 | A | * | 8/1996 | Crainich ...................... | 606/207 |
| 5,582,617 | A | * | 12/1996 | Klieman et al. ............. | 606/170 |
| 5,603,723 | A | * | 2/1997 | Aranyi et al. ................ | 606/205 |
| 5,607,450 | A | * | 3/1997 | Zvenyatsky et al. ......... | 606/206 |
| 5,609,601 | A | * | 3/1997 | Kolesa et al. ................ | 606/170 |
| 5,643,294 | A | * | 7/1997 | Tovey et al. ................. | 606/148 |
| 5,702,408 | A | * | 12/1997 | Wales et al. ................. | 606/139 |
| 5,743,456 | A | * | 4/1998 | Jones et al. .............. | 227/176.1 |
| 5,827,323 | A | * | 10/1998 | Klieman et al. ............. | 606/205 |
| 5,997,565 | A | * | 12/1999 | Inoue .......................... | 606/205 |
| 6,068,647 | A | * | 5/2000 | Witt et al. ................... | 606/205 |
| 6,309,403 | B1 |   | 10/2001 | Minor et al. | |
| 6,666,854 | B1 | * | 12/2003 | Lange .......................... | 606/1 |
| 6,889,116 | B2 | * | 5/2005 | Jinno .......................... | 700/245 |
| 6,936,061 | B2 | * | 8/2005 | Sasaki ......................... | 606/205 |
| 2002/0040217 | A1 | * | 4/2002 | Jinno ........................... | 606/1 |
| 2002/0055758 | A1 | * | 5/2002 | Sasaki ......................... | 606/205 |

FOREIGN PATENT DOCUMENTS

DE        10036108 A1    11/2001

\* cited by examiner

*Primary Examiner*—Michael Peffley
*Assistant Examiner*—Alex Toy
(74) *Attorney, Agent, or Firm*—Mayer, Brown, Rowe & Maw, LLP

(57) ABSTRACT

A surgical instrument comprising a tube shaft at the proximal end of which an instrument head for rotatably supporting an effector is pivotably supported and at the distal end of which an instrument handle is arranged which causes a pivot as well as a bending movement of the instrument head via a bending gear train and a rotation of the effector via a rotation gear train. In the rotation gear train, a motion compensating member is integrated and also is operated via the instrument handle when the bending gear train is operated, and drives the rotation gear train such that an operation of the rotation gear train caused by the pivoting movement of the instrument head, or parts thereof, is compensated.

14 Claims, 5 Drawing Sheets

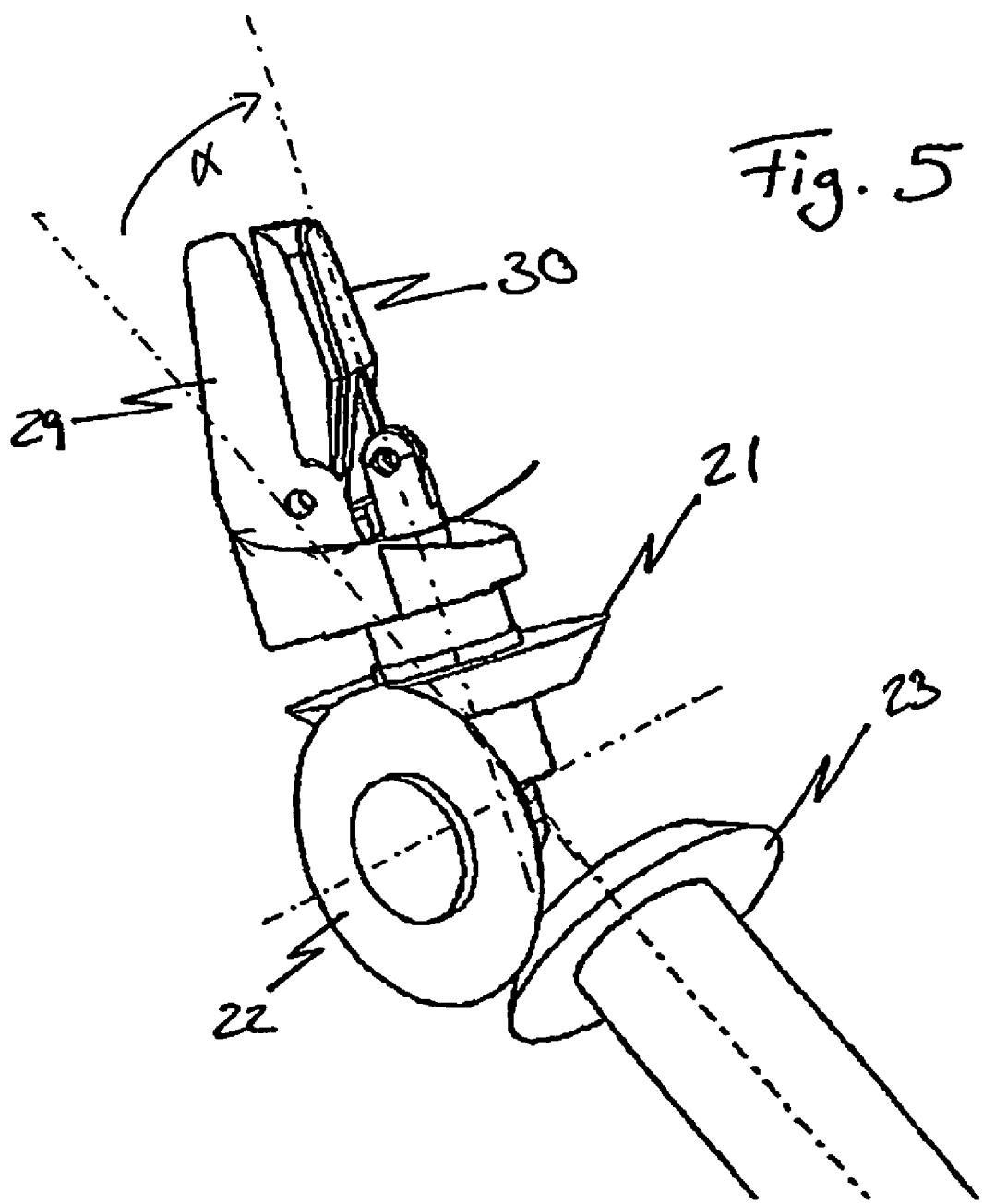

SURGICAL INSTRUMENT

BACKGROUND OF THE INVENTION

1. Field of the Invention

The present invention relates to a surgical instrument for minimally invasive surgery.

2. Discussion of the Prior Art

From DE 100 36 108, a surgical instrument of this generic type is known. It substantially consists of a tube shaft at the one proximal end of which an instrument handle is arranged for the operation of an instrument head disposed at the opposed distal end of the tube shaft via gear trains. The instrument head can be rotated about the longitudinal axis of the tube shaft and can be pivoted and/or inclined with respect to the tube shaft and, moreover, holds an effector in the form of a type of forceps or tongs the one jaw of which is pivotably supported on the instrument head and is operable by means of the instrument handle.

In more concrete terms, the gear trains enable at least a first motion of the instrument handle, for instance to be triggered by rotation of an operator's hand, to be transformed into a rotation of the effector at a predetermined transmission ratio with respect to this operating movement. In this way, it is possible to rotate the effector despite the relatively restricted possibility of motion of a human hand about up to 300°, for instance, and thus to realize complex motions without changing the grip at the handle. Moreover, a second movement of the instrument handle, for instance bending the same with respect to the tube shaft, is converted into an inclination movement of the instrument head.

The gear trains provided inside the instrument handle and the tube shaft are designed such that a most largely decoupled operation of each individual movement of the instrument head and the effector is permitted. However, such gears are necessarily extremely complex and consequently also require sufficient space. Moreover, a complete decoupling of the individual movements is not completely ensured.

In view of this prior art, it is the object of the present invention to provide a surgical instrument of this generic type in which movements of an instrument head can be performed decoupled from each other via an instrument handle.

SUMMARY OF THE INVENTION

This object is achieved by a surgical instrument comprising a tube shaft having an effector rotatably and pivotably supported at one end and at the other end of the tube shaft an instrument handle is arranged for effecting a pivoting movement via a first gear train and a rotational movement of the effector via a second gear train, wherein a motion compensating member is integrated in the second gear train so that a drive of the second gear train caused by a pivoting movement of the effector is compensated when the first gear train is driven by the instrument handle to pivot the effector.

Accordingly, the core of the invention consists in the arrangement of a motion compensating member which is integrated in the rotation gear train and which, when the instrument handle is operated for pivoting the instrument head, drives the rotation gear train simultaneously such that an operation of the rotation gear train caused by the pivoting movement of the instrument head is compensated and, thus, a rotation of the effector supported in the instrument head is prevented. In this way, it is possible to adjust and/or maintain the position of rotation of the effector independently of the respective bending position of the instrument head.

The second gear train preferably consists of the motion compensating member preferably in the form of a long-face pinion which is supported at the pivot axis of the handle member at the tube shaft and which transmits a rotation operation at the handle member to a rotary shaft supported in the tube shaft, the rotary shaft engaging a transmission gear which is supported at a pivot axis of the effector at the tube shaft and which meshes with an output gear attached at a longitudinal axis of the effector. As soon as the handle member is pivoted about the pivot axis for bending the effector, the long-face pinion is also correspondingly rotated and drives the transmission gear via the rotary shaft. Further preferably, the transmission ratio between the long-face pinion and the transmission gear is defined such that when the handle member is pivoted, the angle of rotation of the transmission gear corresponds to the angle of rotation which is performed by the output gear when the effector is bent, so that the relative position between the transmission gear and the output gear is maintained and a forced rotation of the effector does not occur.

This configuration has the advantage that no compensating means in addition to the first and second gear trains have to be provided and, therefore, the entire means can be accommodated in a small assembly space.

Further advantageous developments of the invention are the subject matter of the dependent claims.

BRIEF DESCRIPTION OF THE DRAWINGS

Hereinafter, the invention will be explained in detail by example of a preferred embodiment with reference to the accompanying drawings, in which:

FIG. 5 shows a partial section of the second gear train in the pivoting range of the instrument head.

DETAILED DESCRIPTION OF THE PREFERRED EMBODIMENTS

Figure 1:
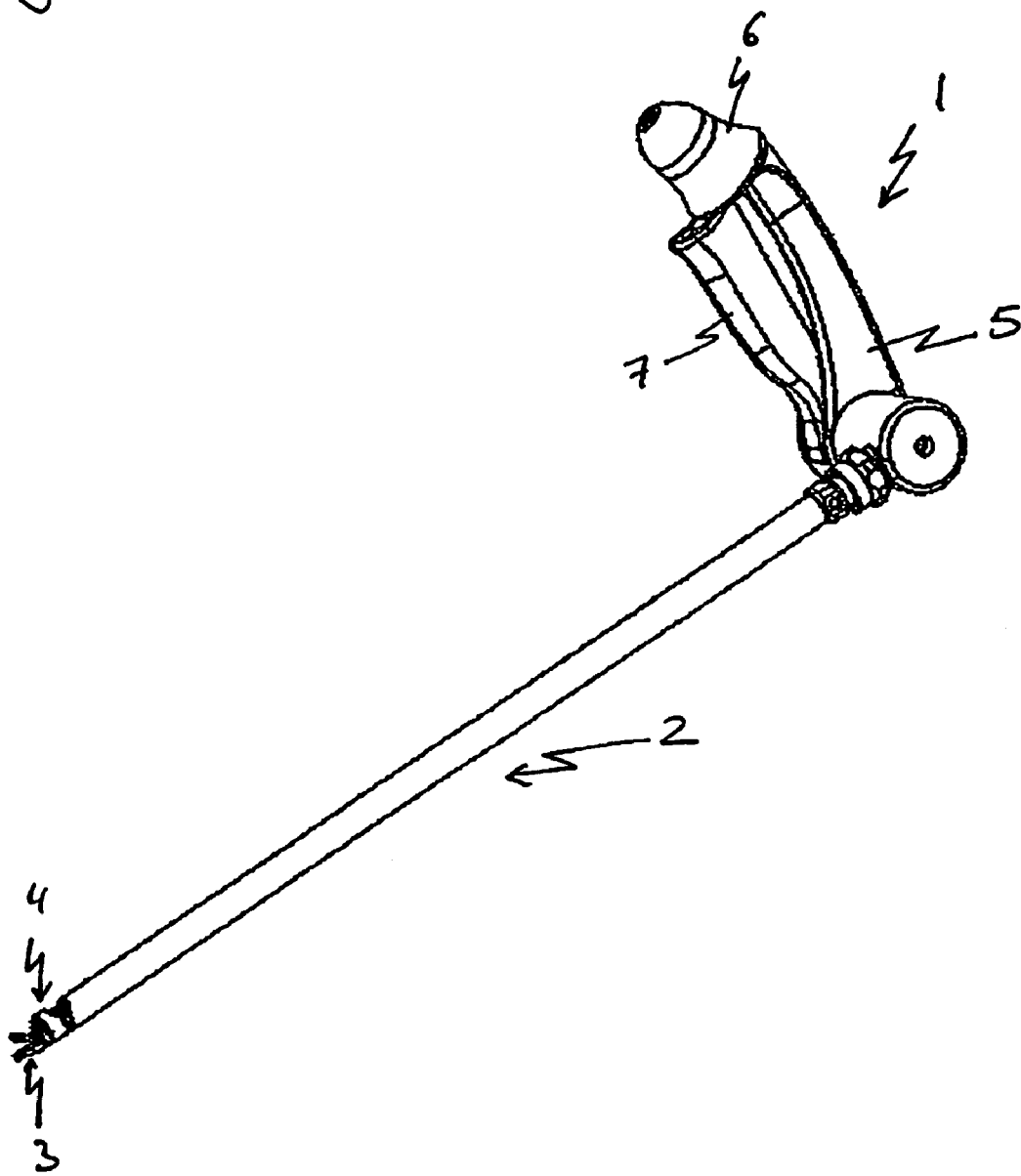
FIG. 1 shows a perspective view of a surgical instrument according to a preferred embodiment of the invention.

In FIG. 1, a complete surgical instrument according to a preferred embodiment of the invention is shown in a perspective view. The surgical instrument according to the invention consequently has a multi-functional instrument handle 1 which is arranged at a proximal end or end portion of a tube shaft 2 preferably made of stainless steel, a steel alloy or a synthetic material as well as an instrument head 4 equipped or adapted to be equipped with an effector 3, the instrument head being provided at the other, distal end of the tube shaft 2.

In general, the instrument head 4 is supported at the respective tube shaft end such that it can be pivoted and/or bent with respect to the tube shaft 2, whereas the effector 3 can be rotated in each bending position of the instrument head 4 about the longitudinal axis of the latter, the two aforementioned motions being adapted to be performed by means of the instrument handle 1. To this end, a number of manipulators or operating mechanisms are provided at the instrument handle 1 and are operatively connected via corresponding gear trains inside the instrument handle 1 as well as inside the tube shaft 2 to the instrument head 4 and the effector 3, respectively, so as to be able to perform the individual motions of the instrument head 4 and of the effector 3 independently of each other, i.e. in a decoupled manner.

Specifically, the instrument handle 1 consists of an ergonomically shaped handle piece 5 which is mounted in a pivotable and inclinable manner to the tube shaft 2 and on which a first manipulator 6, in the present case preferably in the form of a rotary knob, and a second manipulator 7, in the present case preferably in the form of a handle lever, are supported. Thus, the instrument handle 1 according to the preferred embodiment of the present invention comprises a total of three operating mechanisms for three independent movements of the effector 3 and/or the instrument head 4, respectively. It is explicitly emphasized in this context that the instrument handle 1 may also have fewer operation possibilities, for instance only one manipulator or operating mechanism, respectively, for pivoting the instrument head 4 and rotating the effector 3.

Figure 2:
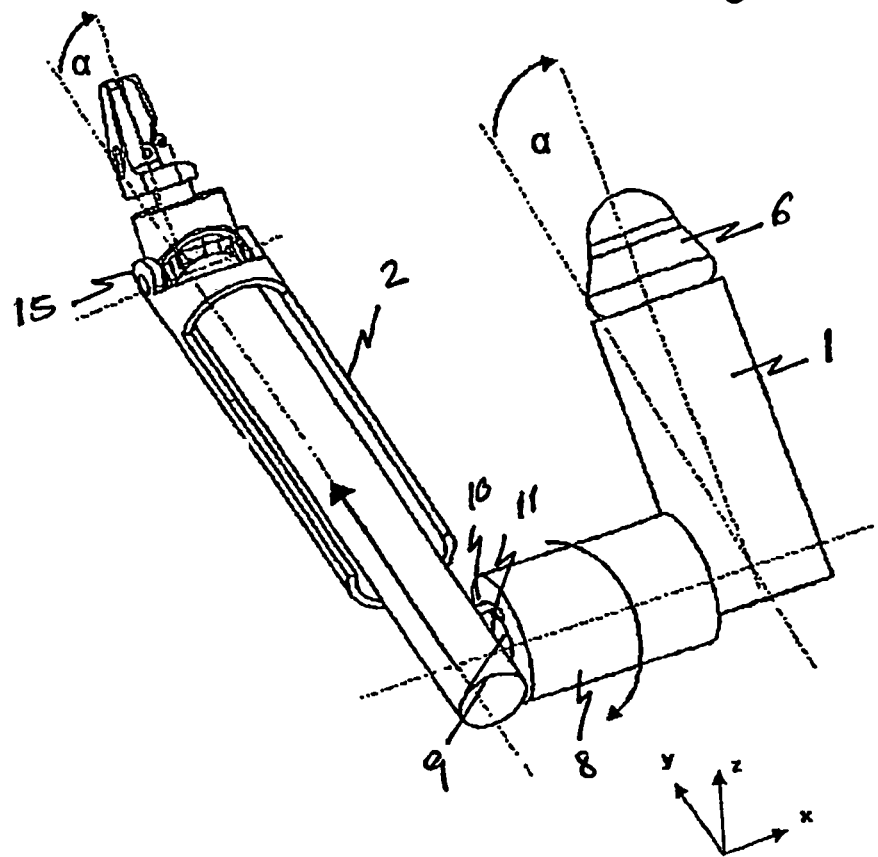
FIG. 2 shows a first gear train for pivoting an instrument head by means of an instrument handle.
Figure 3:
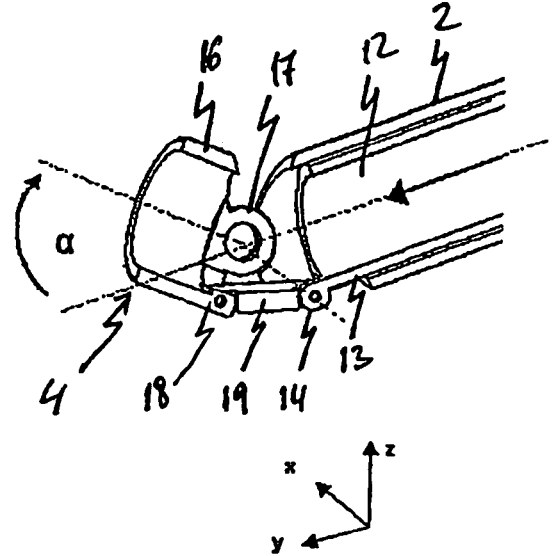
FIG. 3 shows a partial section of the first gear train in the pivoting range of the instrument head.

The exterior structure of the instrument handle 1, especially with respect to the operating mechanism for pivoting and bending the instrument head 4 and with respect to the corresponding bending gear train is illustrated in FIGS. 2 and 3.

The handle 1 schematically shown in FIG. 2 is pivotally connected to the tube shaft 2 via a crank member 8 which is fixedly connected to the handle member 5 and has the form of a rotary shaft or rotary disk. The rotary shaft 8 is preferably aligned to be perpendicular to the tube shaft 2 as well as to the handle member 5 and spaces the handle member 5 from the tube shaft 2 such that the handle 1 can be pivoted substantially in parallel to the tube shaft 2 past the same.

The rotary shaft 8, forming a central through passage 9 for accommodating the gear members described hereinafter, is shaped at its one front facing the tube shaft 2 to have a crank guide 10 in the form of a cam-shaped groove in which a driving pin 11 engages which is attached to an axially movable pushing tube 12 supported in the tube shaft 2. The groove 10 is formed such that, during a rotation of the rotary shaft 8, the driving pin 11 slides along in the groove 10 by an appropriate pivoting of the handle member 5 and, in so doing, performs a forced compensating movement in the longitudinal direction of the tube shaft 2, said movement being transmitted to the pushing tube 12 and resulting in a reciprocating motion of the pushing tube 12 inside the tube shaft 2 depending on the direction of rotation of the rotary shaft 8.

The distal end portion of the pushing tube 12 opposite to the crank member 8 is formed to have a longitudinally extending mounting link 13 which projects from the distal end of the pushing tube 12 and forms a hinge or link eyes 14 at its free end portion. Moreover, the front of the tube shaft 2 is chamfered at its distal end portion at an angle of preferably 45° and includes lateral joint eyes 15 to which the instrument head 4 is pivotally linked via link joints or pins. The instrument head 4 equally consists of a tube member 16 at whose one end control eyes 17 for connection to the tube shaft 2, or rather to the link eyes 15 thereof, are formed is likewise beveled or chamfered at an angle of preferably 45°, namely in such manner that, after linking the instrument head 4 to the tube shaft 2, the two aforementioned bevels complement each other and enable the tube member 16 to be bent with respect to the tube shaft 2 by approximately 90°, preferably 70°.

Moreover, a hinge or rather pivot eyes 18 are formed at the chamfered end of the tube member 16. To each of the link eyes 14; 18 provided at the pushing tube side and the tube member side, a rocking lever 19 is hinged and is consequently offset radially outwardly with respect to the pivot axis of the instrument head 4 and transmits an axial translation movement of the pushing tube 12 to the tube member 16 whereby the latter is pivoted about its own pivot axis.

Figure 4:
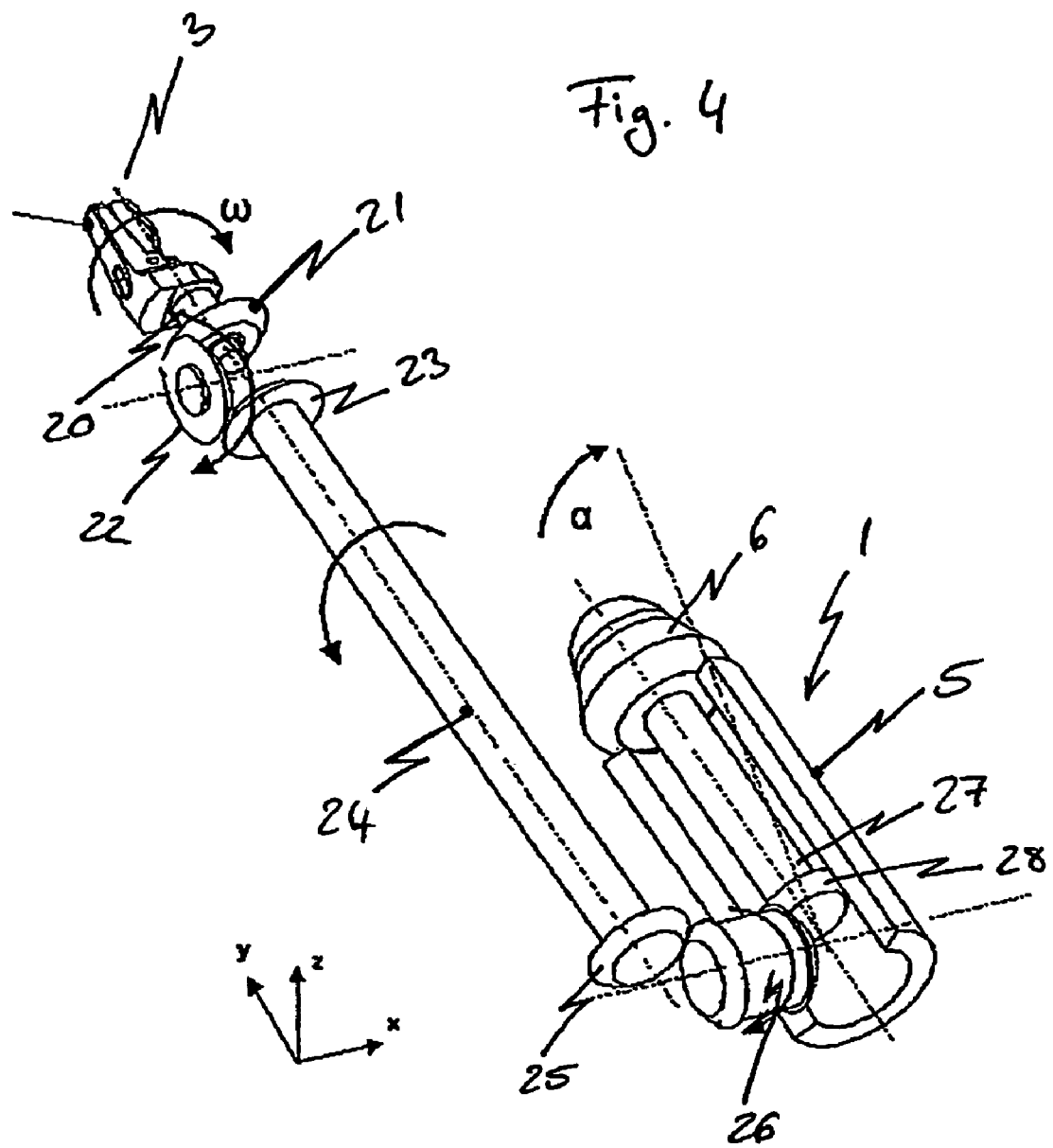
FIG. 4 shows a second gear train for rotation of the instrument head by means of the instrument handle.

Hereinafter, the operating mechanism for a rotation of the effector 3 supported in the instrument head 4 and the corresponding rotation gear train are described by way of FIG. 4 and FIG. 5.

As can further be taken from FIG. 2, the aforementioned tube member 16 of the instrument head 4 at the same time constitutes a housing and/or a receptacle for the effector 3. Independently of the type of effector, i.e. independently of whether for instance a needle holder, tongs, forceps or scissors are used as effector, the latter has a preferably hollow rotational shaft 20 which is rotatably inserted in the tube member 16 of the instrument head 4 and is secured against an axial movement. The length of this rotational shaft is selected such that it ends approximately in the area of the pivot axis of the instrument head 4 and is provided at its free end projecting toward this pivot axis with an output spur gear 21 which is attached to the rotational shaft 20 of the effector 3 in a torque-proof manner. Especially in FIG. 2, the pivot axis of the instrument head 4 is shown by a broken line through the eyes 15.

As can further be taken from FIG. 5, a torque transmission spur gear 22 is provided on the pivot axis of the instrument head 4, is rotatably supported on one of the two pivot pins of the instrument head 4, not shown in detail, which form the pivot axis schematically shown, and is in mesh with the output spur gear 21. The torque transmission spur gear 22 in its turn is in mesh with a drive spur gear 23 which is fixedly mounted on a drive shaft 24 rotatably guided inside the pushing tube 12 (not shown in FIGS. 4 and 5), as this is especially shown in FIG. 4. According to FIG. 4, another torque initiating spur gear 25 is fixedly arranged at one end of the drive shaft 24 opposed to the drive spur gear 23 and is in mesh with a long-face pinion 26 supported in the central through passage 9 formed inside the crank member 8. The crank member 8 is not shown in detail in FIG. 4.

Finally, the long-face pinion 26 is in mesh with an actuating shaft 27 or rather with a spur gear 28 fastened thereto, respectively, inside the handle 1, said shaft being fixedly connected to the one manipulator, the rotary knob 6 in the present case.

When operating the rotary knob 6, the rotation thereof is transmitted via the actuating shaft 27 inside the handle 1, the long-face pinion 26, the subsequent drive shaft 24 inside the pushing tube 12 as well as the transmission spur gear 22 to the effector 3, and the latter is turned. The rotary knob 6 is advantageously operated by the fingers, especially by the thumb and the index of the operator's hand, while the handle member 5 is held in the hand. Thus, it is possible to generate any rotation at the effector 3 without the operator having to change his grip at the handle member 5 itself. In this context, it is further referred to the fact that the drive shaft 24 and the pushing tube 12 are arranged in the axial direction to be relatively movable with respect to each other, i.e., a rotation of the crank member 8 triggered by pivoting the handle 1 does cause a translation movement of the pushing tube 12.

Yet, at the same time, the drive shaft 24 is held in position, i.e. in mesh with the long-face pinion 26, whereby the pushing tube 12 performs an axial relative movement with respect to the tube shaft 2 and to the drive shaft 24.

Ultimately, hereinafter the operating mechanism for the effector 3, i.e. the functions thereof, and for the corresponding effector gear train is described by reference to FIGS. 5 and 6a-6c.

According to FIG. 5, in the present embodiment of the invention, the effector 3 is designed as tongs including a fixed jaw and a movable, i.e. pivoting jaw 29; 30. The fixed jaw 29 forms a unit together with the rotating shaft 20 and is preferably formed integrally with the rotating shaft 20, whereas the movable jaw 30 is linked to the fixed jaw 29 at one end.

The movable jaw 30 forms a linking point 31 for a pushing pin 32 which is supported inside the rotating shaft 20 so as to be relatively shiftable, so that a pivoting movement of the movable jaw 30 with maximum possible transmission is caused by the axial shifting of the pushing pin. As this is especially shown in FIGS. 6a-6c, the pushing pin 32 is biased by a spring 33 axially in the opening direction of the tongs, enclosing the pushing pin 32 inside the rotating shaft 20. For this purpose, the pushing pin 32 has a shaft protrusion at which the biasing spring 33 is supported by its one end. The other end of the biasing spring 33 is supported against the fixed jaw 29. An end piece 34 of the pushing pin 32 projecting from the rotating shaft 20 towards the pivot axis of the instrument head 4 is formed as a ball-shaped head, the radius of the ball-shaped head 34 preferably being approximately 2.5 mm in the present case.

The aforementioned drive shaft 24 for rotating the effector 3 supported in the instrument head 4 is provided with a substantially continuous axial bore (not shown in detail). In this axial bore, a pushing rod 35 is guided to be axially displaceable as well as rotatable relative to the drive shaft 24, the front face of the pushing rod facing the pushing pin 32 being beveled or chamfered in accordance with the bevels of the distal end provided at the tube shaft side and the pushing tube side, i.e. preferably 45° in the same direction. The pushing pin 32 is biased against this chamfered front face of the pushing rod 35 by the spring 33 and abuts against the same. The contact between the pushing rod 35 and the pushing pin 32 is substantially punctiform due to the afore-described ball-shaped head of the pin 32, namely independently of the degree of bending of the instrument head 4 and independently of the position of rotation of the effector 3.

Figures 6A, 6B, 6C:
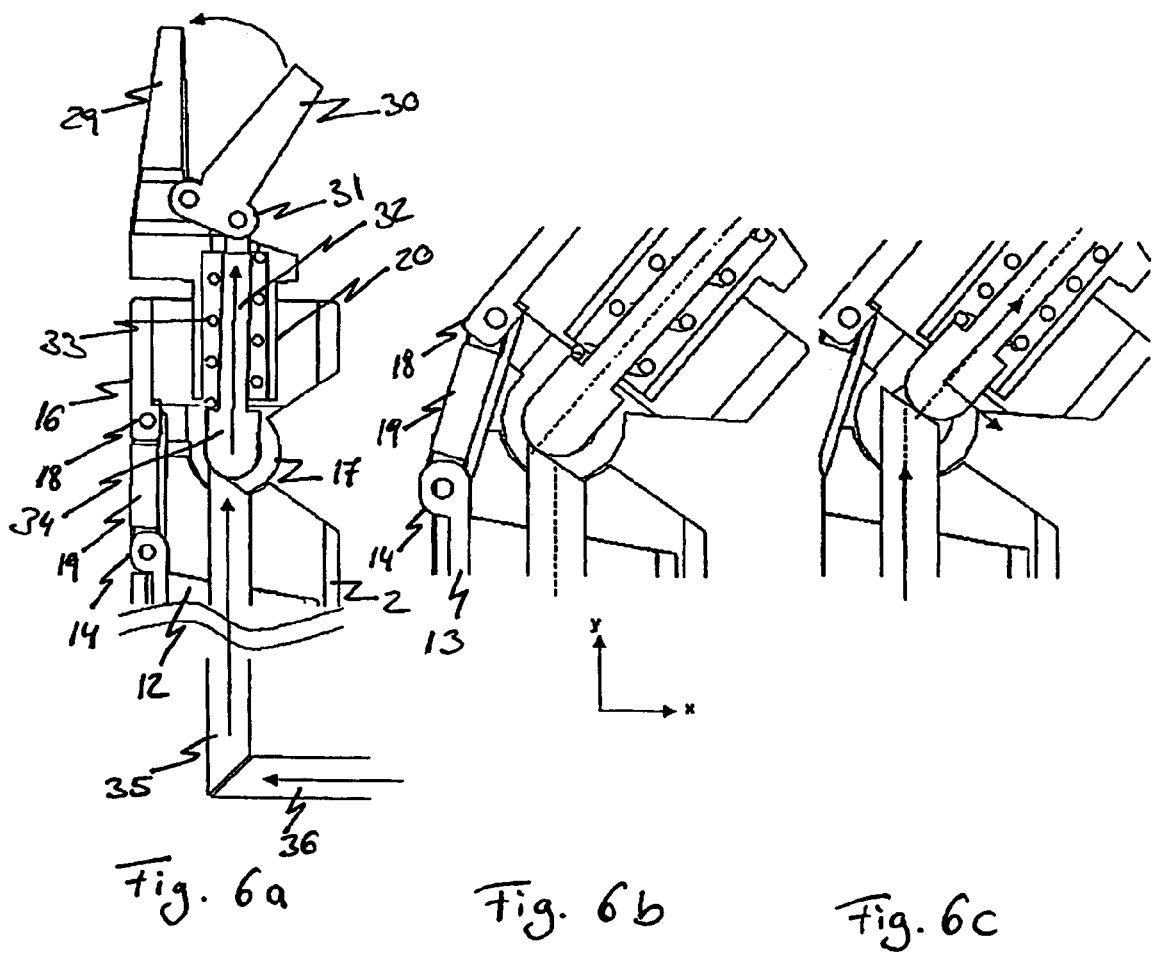
FIG. 6a-6c show sectional views of a third gear train in the pivoting range of the instrument head for the operation of forceps supported at the instrument head.

As can be seen from FIG. 6a, the pushing pin 32 as well as the pushing rod 35 are aligned axially with respect to each other in case that the bending of the instrument head 4 with respect to the tube shaft 2 is substantially 0°. Moreover, in this position of the instrument head 4, the pushing pin 32 is positioned such that the center of the ball head 34 of the pushing pin 32 is located approximately in the pivot axis of the instrument head 4.

At its proximal end, the pushing rod 35 is connected via a gear 36, not shown in detail, to the actuating lever 7 which is pivoted to the handle 1, as already briefly explained at the beginning of this description.

The functioning of the surgical instrument according to the invention will be described hereinafter in detail.

A rotation of the effector 3 supported in the instrument head 4 is effected by an operation of the rotary knob 6 supported at one end of the handle 1, the rotary knob 6 being adapted to be turned about its axis of rotation, as already described in the foregoing, so far that a rotation of approximately 360° is realized for the effector 3 without the necessity to change the grip at the handle member 5. This rotation is transmitted via the actuating shaft 27 to the long-face pinion 26 which, in its turn, transmits its rotation to the drive shaft 24 extending inside the pushing tube 12. The rotation of the drive shaft 24 causes a rotation of the transmission spur gear 22 which quasi bridges the pivot axis of the instrument head 4 and, thus, triggers a rotational movement of the effector 3 inside the tube member 16 of the instrument head 4 about the axis of the tube member.

According to the present embodiment, the entire handle 1 has to be pivoted about the longitudinal axis of the crank member 8 to effect a bending, i.e. a pivoting movement of the instrument head 4 and, thus, of the effector 3. In other words, a pivoting movement of the handle 1 with respect to the tube shaft 2 causes a rotation of the crank member 8 fixedly connected to the handle 1. At the same time, however, the long-face pinion 26 is rotated along with the crank member 8 due to the fact that a kind of automatic lock by friction (efficiency of the gear) occurs by the mesh engagement between the actuating shaft 27 and the long-face pinion 26, said lock being possibly further assisted by slightly holding the knob 6 and by the static friction between the knob 6 and the handle member 5.

The rotation of the crank member 8 is transmitted via the crank or rather groove 10 at the end of the member 8 as well as the driving pin 11 into an axial movement of the pushing tube 12, which is transformed via the hinged rocking lever 19 into a pivoting movement of the instrument head 4 about the pivot axis thereof. However, this pivoting movement is automatically also performed by the output spur gear 21 which is fixed to the rotation axis of the effector 3 and is in mesh with the transmission spur gear 22. If, accordingly, the transmission spur gear 22 were stationary in this kind of operation, i.e. the pivoting operation, the pivoting movement of the instrument head 4 would cause the output spur gear 21 to roll off the transmission spur gear 22 in the same direction and, thus, would inevitably result in a superimposed motion of rotation of the effector 3.

As described in the foregoing, however, the long-face pinion 26 is rotated along with the crank member 8 during a pivoting movement of the handle member 1 and thus drives the drive shaft 24 inside the pushing tube 12. The transmission between the long-face pinion 26 and the drive shaft 24 is calculated such that the transmission gear 22 is rotated by the drive shaft 24 about such an angle of rotation corresponding to the angle of rotation which is caused by the output gear 21 during a corresponding bending of the instrument head 4, whereby both rotations compensate each other due to their counter-rotation. In this configuration the relative position between the transmission spur gear 22 and the output spur gear 21 is maintained even during the bending motion of the instrument head 4, so that the effector 3 is held in each bending position of the instrument head 4 and during a bending motion, as well as in its current position of rotation with respect to the instrument head 4.

In order to effect the operation of the effector 3, i.e. the function thereof itself, the lever 7 pivoted to the handle member 5 is provided in the present preferred embodiment. As already described in the foregoing concerning FIGS. 6a-6c, lever 7 is operatively connected via a reversing gear not shown in detail or an appropriate joint mechanism to the pushing rod 35 which is supported in the rotary shaft 24 and which axially reciprocates relative to the rotary shaft 24 upon a corresponding operation of the lever 7. A simple Bowden cable or deflecting lever would also be conceivable for a power transmission to the pushing rod 35.

FIG. 6a shows the relative position of the pushing rod 35 and the pushing pin 32 in a bending position of the instrument head 4 of 0° with the tongs being opened, FIG. 6b shows the relative position of the pushing rod 35 and the pushing pin 32 in a bending position of the instrument head 4 of approximately 45° with the tongs being opened, and FIG. 6c shows the relative position of the pushing rod 35 and the pushing pin 32 in a bending position of the instrument head 4 of approximately 45° with the tongs being closed.

As one can take from FIGS. 6a-6c, the pushing pin 32 is kept in constant contact with the chamfered or chamfered distal front of the pushing rod 35 by the biasing force of the spring 33. When the pushing rod 35 is displaced in the direction of the instrument head 4 in the case of a 0° bending of the instrument head 4 according to FIG. 6a, the pushing pin 32 is displaced at the same speed and over the same distance as the pushing rod 35, i.e. without transmission, against the biasing force of the spring 33, whereby the jaw 30 of the tongs linked thereto is pivoted in the closing direction.

In this context, it is referred to the fact that by the displacing action of the pushing rod 35, the pushing pin 32, i.e. especially the center of the pin head radius, remains only approximately on the pivot axis of the instrument head 4, i.e. it moves in a kind of orbit during a bending motion of the instrument head 4. As already explained in the beginning of the description of the figures, however, the regulating distances for opening and closing the tongs, for instance, are so small due to the transmissions set that the orbit radius can be calculated theoretically, but it has no relevant influence on the position of the tongs for reasons of manufacture already (natural elasticity of the materials used, dimensional tolerances and play at the link joints and gear parts). In other words, the position of the tongs is determined by the position of the lever 7 which, in its turn, is held by an operator and, thus, is subjected, for instance, to noncontrollable movements of the hand (trembling motions). Such disturbances produced due to manual operations are greater by far and, therefore, practically only relevant compared to the disturbances produced by the afore-described orbit motion.

That is to say, irrespective of the current position of the pushing rod 35 and the pushing pin 32, respectively, a bending of the instrument head 4 does generally not only cause the pushing pin 32 to pivot with respect to the pushing rod 35 but also causes the pin head 34 to slightly slide off the chamfered front face of the pushing rod 35. By this little slide-off motion, the bearing contact of the pushing pin 32 with the front face is maintained, wherein only such a compensating longitudinal motion of the pushing pin 32 takes place as a result of its slide-off motion, however, which entails no practically relevant change of the closing or opening position at the effector 3. At the same time, however, a kind of power deflection mechanism is provided so as to bring about a longitudinal motion of the pushing rod 35 into a longitudinal motion of the pushing pin 32 now provided at an angular position with respect to the pushing rod 35 by the beveling or chamfering of the front of the pushing rod.

In other words, if the pushing rod 35 is displaced in a bending position >0° according to FIG. 6b in the closing direction of the effector 3, as illustrated in FIG. 6c, the chamfered front face of the pushing rod 35 slides longitudinally past the pin head 34 and thus exerts an advance force on the pushing pin 32 which accordingly moves in the closing direction of the effector 3.

To sum up, an inventive idea may hence be described as a surgical instrument comprising a tube shaft 2 at the proximal end of which an instrument head 4 rotatably supporting an effector 3 is pivoted and at the distal end of which an instrument handle 1 is arranged and effects a pivoting and bending motion, respectively, of the instrument head 4 via a bending gear train and a rotation of the effector 3 via a rotation gear train. A motion compensating element, preferably in the form of a long-face pinion 26, is integrated in the rotation gear train, the motion compensating element being operated along with the operation of the bending gear train via the instrument handle 1 and driving the rotation gear train such that an operation of the rotation gear train caused by the pivoting movement of the instrument head 4, or parts thereof, is/are compensated.

It should be understood that any of a variety of fastening means and suitable materials of construction and dimensions may be used to satisfy the particular needs and requirements of the end user. It also will be apparent to those skilled in the art that various modifications and variations can be made in the design and construction of a surgical instrument without departing from the scope or spirit of the invention.

I claim:

1. A surgical instrument comprising a tube shaft having an effector rotatably and pivotably supported at one end and at the other end of the tube shaft an instrument handle is arranged for effecting a pivoting movement via a first gear train and a rotational movement of the effector via a second gear train, wherein a motion compensating member is integrated in the second gear train so that a drive of the second gear train caused by a pivoting movement of the effector is compensated when the first gear train is driven by the instrument handle to pivot the effector.

2. A surgical instrument according to claim 1, wherein the instrument handle comprises a first pivot operating mechanism operatively connected to the first gear train and comprises a rotation operating mechanism operatively connected to the second gear train, the first gear train and second gear train being operable independently of each other to respectively rotate the effector supported in an instrument head and to bend the instrument head together with the effector.

3. A surgical instrument according to claim 2, wherein the motion compensating member can be driven by the instrument handle, by the rotation operating mechanism and by the pivot operating mechanism simultaneously.

4. A surgical instrument according to claim 2, wherein the pivot operating mechanism includes a pivot bearing of the instrument handle at the tube shaft in which the motion compensating member is arranged in the form of a long-face pinion so that it is rotatable by a pivoting movement of the instrument handle for driving the second gear train.

5. A surgical instrument according to claim 4, wherein the second gear train includes the motion compensating member which also is a part of the rotation operating mechanism of the instrument handle that transmits a rotation operation to a rotary shaft supported in the tube shaft, and the rotary shaft engaging a transmission gear which is supported at a pivot axis of the effector at the tube shaft and meshes with an output gear attached at a longitudinal axis of the effector.

6. A surgical instrument according to claim 5, wherein the first gear train includes a crank element which forms a pivot bearing of the instrument handle and which is connected in a torque-proof manner to the instrument handle and engages a pushing tube supported in the tube shaft so as to transform a pivoting movement of the instrument handle into an axial movement of the pushing tube and which, at its end facing the instrument head, is operatively connected to the instrument head via a joint mechanism so as to pivot the instrument head during an axial shifting about its pivot axis with the tube shaft.

7. A surgical instrument according to claim 6, wherein the crank element is in the form of a rotary shaft at one end of which a crank consisting of a groove-shaped cam path is formed, in which a driving pin attached to the pushing tube engages.

8. A surgical instrument according to claim 3, wherein the pivot operating mechanism includes a pivot bearing of the instrument handle at the tube shaft in which the motion compensating member is arranged in the form of a long-face pinion so that it is rotatable by a pivoting movement of the instrument handle for driving the second gear train.

9. A surgical instrument according to claim 8, wherein the second gear train includes the motion compensating member which also is a part of the rotation operating mechanism of the instrument handle that transmits a rotation operation to a rotary shaft supported in the tube shaft, and the rotary shaft engaging a transmission gear which is supported at a pivot axis of the effector at the tube shaft and meshes with an output gear attached at a longitudinal axis of the effector.

10. A surgical instrument according to claim 9, wherein the first gear train includes a crank element which forms a pivot bearing of the instrument handle and which is connected in a torque-proof manner to the instrument handle and engages a pushing tube supported in the tube shaft so as to transform a pivoting movement of the instrument handle into an axial movement of the pushing tube and which, at its end facing the instrument head, is operatively connected to the instrument head via a joint mechanism so as to pivot the instrument head during an axial shifting about its pivot axis with the tube shaft.

11. A surgical instrument according to claim 10, wherein the crank element is in the form of a rotary shaft at one end of which a crank consisting of a groove-shaped cam path is formed, in which a driving pin attached to the pushing tube engages.

12. A surgical instrument according to claim 5, wherein the rotation operating mechanism consists of a manipulator supported at the instrument handle and having the form of a rotary knob which is connected to an actuating shaft supported in the handle and operatively connected to the long-face pinion via a gear mechanism.

13. A surgical instrument according to claim 12, wherein the transmission ratio of the gear mechanism is defined such that when the instrument handle is pivoted about any angle $\alpha$, which causes bending of the instrument head at about an angle $\alpha$, the rotary shaft is rotated about such an angle that the transmission gear supported on the pivot axis of the instrument head is rotated about the same angel $\alpha$ as the instrument head, whereby the relative position between the transmission gear and the output gear remains unchanged.

14. A surgical instrument according to claim 5, wherein the rotation operating mechanism consists of a manipulator supported at the instrument handle and having the form of a rotary knob which is connected to an actuating shaft supported in the handle and operatively connected to the long-face pinion via a gear mechanism.

* * * * *